(12) United States Patent
Winkelstein et al.

(10) Patent No.: US 9,808,514 B2
(45) Date of Patent: Nov. 7, 2017

(54) METHOD OF USING SALMON THROMBIN TO ALLEVIATE CENTRAL NERVOUS SYSTEM-MEDIATED PAIN

(75) Inventors: Beth A. Winkelstein, Freeport, ME (US); Paul A. Janmey, Freeport, ME (US); Evelyn S. Sawyer, Freeport, ME (US)

(73) Assignee: Sea Run Holdings, Inc., Freeport, ME (US)

( * ) Notice: Subject to any disclaimer, the term of this patent is extended or adjusted under 35 U.S.C. 154(b) by 1580 days.

(21) Appl. No.: 12/582,040

(22) Filed: Oct. 20, 2009

(65) Prior Publication Data

US 2010/0111926 A1 May 6, 2010

Related U.S. Application Data

(60) Provisional application No. 61/111,828, filed on Nov. 6, 2008.

(51) Int. Cl.
*A61K 38/48* (2006.01)
*C12N 9/74* (2006.01)

(52) U.S. Cl.
CPC ................. *A61K 38/4833* (2013.01)

(58) Field of Classification Search
None
See application file for complete search history.

(56) References Cited

U.S. PATENT DOCUMENTS

2006/0095016 A1* 5/2006 Pauza et al. .................. 604/512
2012/0009175 A1* 1/2012 Sawyer et al. ............. 424/94.64

OTHER PUBLICATIONS

Ju et al. Enhanced neurite growth from mammalian neurons in three-dimensional salmon fibrin gels. Jan. 26, 2007. Biomaterials. vol. 28, pp. 2097-2108.*
Michaud et al. Purification of salmon thrombin and its potential as an alternative to mammalian thrombins in fibrin sealants. 2002. Thrombosis Research. vol. 107, pp. 245-254.*
Wang et al. Purification of Salmon Clotting Factors and Their Use as Tissue Sealants, Thrombosis Research, vol. 100, 2000, p. 537-548.*
Yin et al. Neurotrophin-4 delivered by fibrin glue promotes peripheral nerve regeneration. 2001. Muscle Nerve. vol. 24, pp. 345-351.*
Manseth et al. Developing a Fish Meat-binding Agent: Purification of Salmon Thrombin. 2003. Journal of Food Science. vol. 68, No. 5, pp. 1648-1652.*
Ondarza et al., Direst evidence of primary afferent sprouting in distant segments following spinal cord injury in the rat: colocalization of GAP-43 and CGRP, Experimental Neurology, 2003, pp. 373-80, vol. 184, issue 1.
Bareiss et al., Excitotoxic spinal cord injury induced dysesthesias are associated with enhanced intrinsic growth of sensory neurons, Neuroscience Letters, 2013, pp. 113-117, vol. 542.

* cited by examiner

*Primary Examiner* — Channing S Mahatan
(74) *Attorney, Agent, or Firm* — IP Strategies

(57) ABSTRACT

A method of alleviating central nervous system-mediated pain includes applying salmon thrombin at a neural injury site. Applying salmon thrombin can include applying a gel that includes salmon thrombin. The gel can also include fibrinogen, for example, salmon fibrinogen, human fibrinogen, or bovine fibrinogen. The salmon thrombin can be obtained from salmon plasma, or using recombinant technology, or by fractionation. A pain relief substance includes a gel that includes salmon thrombin.

22 Claims, 2 Drawing Sheets

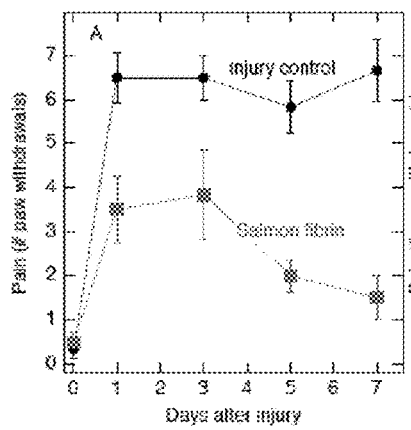
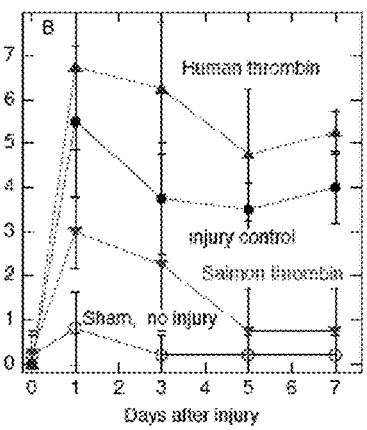
Fig. 1A                Fig. 1B
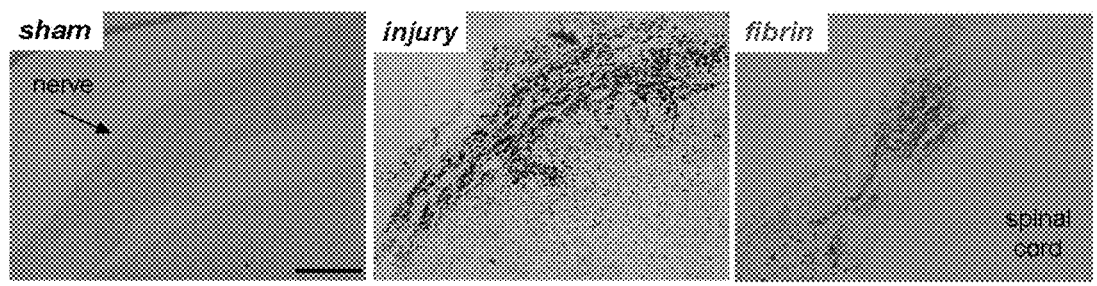
Fig. 2

METHOD OF USING SALMON THROMBIN TO ALLEVIATE CENTRAL NERVOUS SYSTEM-MEDIATED PAIN

CROSS-REFERENCE TO RELATED APPLICATION

Claim is made of the benefit of the filing date of U.S. Provisional Patent Application No. 61/111,828, filed on Nov. 6, 2008, pursuant to 35 U.S.C. §119(e).

STATEMENT REGARDING FEDERALLY SPONSORED RESEARCH OR DEVELOPMENT

This invention was made with Government support under NIH-SBIR Grant 5-R44NSO48734-03 awarded by the National Institute of Health. The Government has certain rights in this invention.

FIELD OF THE INVENTION

The invention relates to a therapeutic intervention to reduce central nervous system (CNS)-mediated pain.

BACKGROUND OF THE INVENTION

Significant pain in cases of spinal cord injury (SCI) or traumatic brain injury (TBI) is quite common, with an estimated 52-58% of TBI patients reporting chronic pain (Sherman et al. 2006). Headache is the most common symptom, but symptoms suggestive of neuropathic pain are also common, sometimes extending into the neck and regions of the shoulder and back (Uomoto et al. 1993). In this study, pain after TBI occurred in more than one area of the body in 60% of patients. Similarly, in spinal cord injury, around 40% of patients develop persistent neuropathic pain (Baastrup & Finnerup 2008; Yezierski 2005). Neuropathic pain is characterized by spontaneous persistent pain and a range of abnormally-evoked responses, such as allodynia (pain evoked by non-noxious stimuli), and hyperalgesia (an enhanced response to noxious stimuli).

A very common cause of CNS-mediated responses contributing to neuropathic pain is cervical or lumbar nerve root injury (radiculopathy), often a result of whiplash or disc herniation. Nerve roots sit at the junction of the central and peripheral nervous systems (PNS) and contain elements of both nervous systems (Fraher et al. 1987). Both radiculopathic and neuropathic injuries affect cellular mechanisms both locally at the site of injury (that is, the nerve root or nerve), and centrally in the spinal cord. Moreover, the CNS (brain and spinal cord) has been shown to mount cellular and molecular cascades in response to neuropathic and radiculopathic injuries that reflect a perceived injury to the CNS (Hashizume et al. 2000; DeLeo & Yezierski 2001; DeLeo & Winkelstein 2002; Watkins & Maier 2005). Therefore, CNS-mediated pain includes pain with injury originating in the CNS, although it can include pain from injuries that originate in the PNS.

There is a substantial literature on possible interventions, including pharmacological (Basstrup & Finnerup 2008) and physical (acupuncture, heat, electrical) treatments (Kumar et al. 2007). However, all these methods have proved inadequate, and no safe, effective method to treat pain after CNS-mediated responses to neuronal injury has been developed.

Neuropathic pain after CNS injury can have different causes, but activation of microglia and the resulting NO production, and release of pro-inflammatory cytokines is a common mechanism (Huselbosch 2008; Rothman et al 2009b). In addition to its pro-coagulant properties, activation of microglia is one of the many properties of mammalian thrombin, a multifunctional serine protease (Weinstein et al. 2008). Since activation of microglia predicts neuropathic pain, the exposure of CNS tissue to thrombin is contraindicated although it is inevitably produced as a result of blood coagulation subsequent to traumatic injury. Xue et al. (2006) show that thrombin from intracerebral injection of autologous blood in mice produced significant brain damage. Further evidence of thrombin's neurotoxicity on CNS tissue is the neuroprotective effect of thrombin inhibitors (Festoff et al. 2004).

The primary structure of thrombins from various species is highly conserved (Banfield & MacGillivray, 1992). Michaud et al. (2002) compared human and salmon thrombin, and found that they were nearly identical in polymerizing fibrinogen and activating Factor XIII, and similar but not identical in stimulating human platelets. They differed in the greater activity of salmon thrombin at low pH and high salt environments. Sawyer et al. (1999), Wang et al. (2000), and Laidmae et al. (2006) demonstrated the similarity of salmon and mammalian-derived thrombin and fibrinogen as fibrin sealants. When combined with fibrinogen, mammalian thrombin appeared safe for use in the rat CNS (Petter-Puchner et al. 2007), but there was no attenuation of the inflammatory response, and its capability to cause pain was unexamined. Fibrin gels composed of salmon fibrinogen and either human or salmon thrombin were equally effective in enhancing neurite outgrowth from mammalian neurons, and Ju et al. (2007) identified salmon fibrinogen, which differs in amino acid sequence and glycosolation from mammalian fibrinogen, as the beneficial component.

BRIEF SUMMARY OF THE INVENTION

According to an aspect of the invention, a method of alleviating central nervous system-mediated pain includes applying salmon thrombin at a site of neural injury. For example, the neural injury site can be part of the central nervous system and/or part of the peripheral nervous system.

Applying salmon thrombin can include applying a gel that includes salmon thrombin. The gel can also include fibrinogen, for example, salmon fibrinogen, human fibrinogen, or bovine fibrinogen. Alternatively, or in addition, the gel can include polyethylene glycol, a synthetic molecule preparation, collagen, and/or alginates.

Applying the gel can include injecting the gel.

The salmon thrombin can be obtained using any known method from any salmon stock. For example, the method can also include obtaining a salmonid, for example, an Atlantic salmon, that is a progeny of domesticated broodstock that are reared under consistent and reproducible conditions. Blood is obtained from the fish, plasma is separated from the blood, and the salmon thrombin is extracted from the plasma. The salmonid from which the blood can be obtained, for example, sexually immature, in the log-phase of growth, larger than two kilograms, and/or reared by standard husbandry methods. Obtaining blood from the salmonid can include rendering the salmonid to a level of loss of reflex activity and drawing blood from a caudal blood vessel. Prior to rendering the salmonid to a level of loss of reflex activity, the levels of proteolytic enzymes and non-protein nitrogen present in the blood of the salmonid can be reduced. Separating plasma from the blood can include centrifuging the blood. Extracting the salmon fibrin from the plasma can include performing an extraction process on the plasma such that all process temperatures are no greater than 6° C., no cytotoxic chemical residues remain in the one or more plasma components, and no oxidation of plasma lipids occurs. An antioxidant and/or a protease inhibitor can be added to the plasma prior to extracting the salmon thrombin.

Alternatively, the salmon thrombin can be obtained using recombinant technology, or by fractionation.

According to another aspect of the invention, a pain relief substance includes a gel that includes salmon thrombin. The gel can also include fibrinogen, such as salmon fibrinogen, human fibrinogen, or bovine fibrinogen. Alternatively, or in addition, the gel can include polyethylene glycol, a synthetic molecule preparation, collagen, and/or alginates.

BRIEF DESCRIPTION OF THE DRAWINGS

FIG. 1 are charts showing mechanical allodynia in the forepaw following nerve root compression, with FIG. 1A showing results from treatment with salmon fibrin and FIG. 1B showing results from treatment with human and salmon thrombin.

FIG. 2 is a series of representative micrographs showing ED1 staining of macrophages at the C7 ipsilateral nerve root at day 7 after sham controls, injury, and injury with salmon fibrin (thrombin plus fibrinogen) treatment.

DETAILED DESCRIPTION OF THE INVENTION

Figure 3:
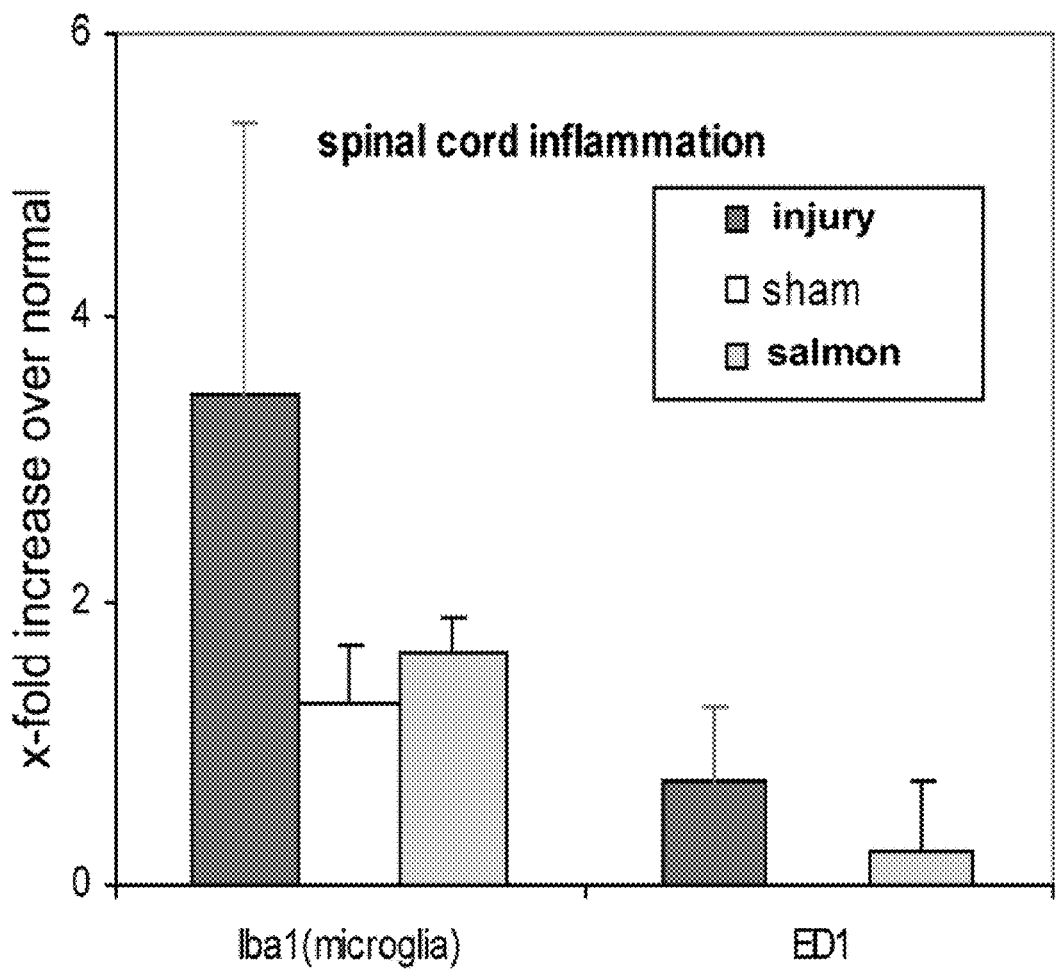
FIG. 3 is a chart showing the activation of microglia (macrophages) by iba1 staining and ED1 staining in the spinal cord adjacent to the injury site.

According to the invention, salmon thrombin is used to significantly reduce pain after neural injury, such as injury to the CNS or PNS, a result that is not possible using mammalian thrombin. The invention utilizes salmon thrombin, a serine protease with molecular weight and enzymatic activities toward coagulation substrates similar to human thrombin. Preferably, the salmon thrombin is obtained from salmon by the methods of Michaud et al. (2002), but may be prepared by any of the well-known commercial methods for preparation of human thrombin such as fractionation (Miller-Andersson et al. 1980) or recombinant technology (Holly et al. 1995). Fibrinogen, preferably from salmon (Wang et al. 2000) or from human or bovine sources using known methods of preparation may be combined with the thrombin.

We used a rat model of mechanical allodynia (behavioral sensitivity) that is generally accepted as mimicking or correlating to human neuropathic pain, and initiating sustained CNS responses that regulate pain originating from injury to the CNS and PNS (DeLeo & Winkelstein, 2002) Hubbard and Winkelstein 2005, 2008; Rothman et al. 2005, 2007, 2009 a,b). We show that injection of salmon fibrinogen and thrombin as a fibrin gel, reduces neuropathic pain after a painful nerve root compression injury. Unexpectedly, we found that salmon thrombin alone, but not human thrombin, produced even greater pain reduction.

Although salmon thrombin may be used alone, it is preferably applied with fibrinogen. The use of fibrinogen offers the benefit of application of both proteins in liquid form with the resulting gel filling the injury site. The gel permits a localized treatment without the concerns that accompany systemic therapy. The thrombin may also be combined with any gel-forming material that is compatible with neural injury repair, such as but not limited to polyethylene glycol, synthetic molecules, collagen, alginates, and other organic molecules and biopolymers.

Example #1

Salmon thrombin was prepared from salmon plasma by the method of Michaud et al, 2002, which is incorporated herein by reference. Salmon fibrinogen was also prepared from salmon plasma by the methods of Wang et al, 2000, which is also incorporated herein by reference. These proteins were lyophilized and then held at less than −20° C. On the day of use, the proteins were rehydrated at room temperature, and then held on ice.

Anesthetized male Sprague-Dawley rats (250-350 g) were subjected to a 15-minute compression of the C7 cervical dorsal nerve root with a 10 gf microclip, an established technique that produces behavioral sensitivity that persists for 3-6 weeks and mimics symptoms of persistent pain (Hubbard et al. 2005). Two groups of rats (N=6 per group) were used to evaluate the effectiveness of the fibrin gel and its components to alleviate pain. In one group of rats no treatment was given at the time of injury. A second group received a fibrin gel prepared from salmon fibrinogen and thrombin at the injury site. The fibrinogen was diluted to a working solution of 6 mgs/ml in low-glucose DMEM (Invitrogen, Inc., Grand Island, N.Y.). Salmon thrombin was also diluted with DMEM to a working solution of 4 NIH units/ml and kept on ice until use. Both proteins were filtered to 0.22μ. Immediately following the compression injury to the nerve root, 20 μl of the fibrinogen solution was pipetted into 20 μl of the thrombin solution, mixed gently, and 20 μl of the fibrin solution was applied directly to the nerve root at the site where the nerve root enters the spinal cord. The fibrin solution was allowed to gel for one minute before the surgical site was sutured. Rats in both groups were followed for seven days, during which time mechanical allodynia was measured in the affected forepaw. Mechanical allodynia was assessed by measuring frequency of paw withdrawals after light touch. Treatment with the salmon-derived fibrin gel significantly decreased behavioral sensitivity in the affected forepaw compared to that of untreated rats (p<0.01) (FIG. 1.). In addition, similar decreases in sensitivity were also observed in the contralateral paw, suggesting a potential utility for reducing widespread symptoms of pain.

Example #2

A second study was performed on several groups of rats to investigate mechanisms by which the salmon fibrin was mediating pain relief in this model. Separate groups underwent nerve root compression, each with one of the following treatments: human thrombin, salmon thrombin, medium alone (neural basal media), or no treatment. The effect on pain reduction was mediated by the activity of salmon thrombin but not human thrombin, as shown in FIG. 1. The charts of FIG. 1 show levels of mechanical allodynia in the forepaw following nerve root compression. FIG. 1A shows that salmon fibrin (thrombin plus fibrinogen) alleviated a measure of pain symptoms; reduction in sensitivity was significant and sustained. FIG. 1B shows that a similar reduction in pain is achieved by salmon thrombin alone but not by human thrombin. Error bars show standard deviation.

The nerve root compression injury does not induce massive bleeding, and the endogenous coagulation factors of the rat are sufficient for hemostasis, but as discussed before, also activate inflammation. Additional clotting activity provided by human thrombin at the site of injury did not alleviate pain compared to medium alone (control), and may even exacerbate the pain response. In contrast, salmon thrombin significantly reduced pain (p<0.005) on all days after treatment. Allodynia after salmon thrombin treatment is statistically indistinguishable from uninjured controls.

Behavioral results showing decreased allodynia after treatment with salmon thrombin alone or combined with salmon fibrinogen given at the site of neural injury demonstrate that the nociceptive and/or inflammatory response is mediated by the salmon thrombin. The neural basal media also decreased allodynia at later time points but to a lesser extent than did the salmon proteins. FIG. 2 is a series of representative micrographs showing ED1 staining of macrophages at the C7 ipsilateral nerve root at day 7 after sham controls, injury, and injury with salmon fibrin (thrombin plus fibrinogen) treatment. As shown, treatment with the salmon fibrin at the time of injury reduced ED1 staining compared to injury. The 100 μm scale bar applies to all micrographs.

Thus, FIG. 2 shows the decreased activation of microglia (macrophages) after treatment with salmon thrombin plus fibrinogen, within the area surrounding the nerve root as evidenced by reduced ED1 staining. This same reduction in ED1 positive cells after treatment was even more pronounced when evaluating the spinal cord, as shown in FIG. 3. FIG. 3 is a chart showing the activation of microglia (macrophages) by iba1 staining and ED1 staining in the spinal cord adjacent to the injury site. As shown, the activation of microglia shown by ED1 staining is reduced after salmon thrombin treatment. Similarly, density of activated microglia as shown by iba1 staining is reduced to sham levels.

Some ED1 staining was present in the spinal cord of all untreated rats, while none was present for sham. However, in the salmon group, only one rat exhibited any ED1 staining in the spinal cord (FIG. 3.). Similarly, using immunohistochemistry (Rothman et al. 2009b), quantitative densitometry indicated a marked reduction of iba1 (another marker of activated microglia) in the spinal cord with staining reduced to sham levels.

These examples address nerve-root pain, a model of CNS-mediated pain with a causative mechanism common to other injuries to the CNS, namely, activation of microglia. An equivalent mechanism in the PNS is activation of Schwann cells (Campana W M, 2007). Therefore, salmon thrombin is likely to show efficacy in the PNS for indications involving pain.

The invention claimed is:

1. A method of alleviating central nervous system-mediated pain, comprising applying salmon thrombin at a neural injury site, thereby diminishing a degree of nerve sensitivity to pain experienced at the site, wherein diminishing a degree of nerve sensitivity to pain experienced at the site includes reducing an inflammatory response at the site.

2. The method of claim 1, wherein the neural injury site is part of the central nervous system.

3. The method of claim 1, wherein the neural injury site is part of the peripheral nervous system.

4. The method of claim 1, wherein applying salmon thrombin includes applying a gel that includes salmon thrombin.

5. The method of claim 4, wherein the gel also includes fibrinogen.

6. The method of claim 5, wherein the fibrinogen is salmon fibrinogen.

7. The method of claim 4, wherein the gel also includes any one or more of polyethylene glycol, a synthetic molecule preparation, collagen, and alginates.

8. The method of claim 4, wherein applying the gel includes injecting the gel.

9. The method of claim 1, further comprising obtaining the salmon thrombin using recombinant technology.

10. The method of claim 1, further comprising obtaining the salmon thrombin by fractionation.

11. The method of claim 1, wherein applying salmon thrombin at the neural injury site comprises applying salmon thrombin at the neural injury site as the only blood component.

12. A method of alleviating central nervous system-mediated pain, comprising applying salmon thrombin at a neural injury site, thereby diminishing a degree of nerve sensitivity to pain experienced at the site, wherein diminishing a degree of nerve sensitivity to pain experienced at the site includes reducing activation of microglia at the site.

13. The method of claim 12, wherein the neural injury site is part of the central nervous system.

14. The method of claim 13, wherein the neural injury site is part of the peripheral nervous system.

15. The method of claim 13, wherein applying salmon thrombin includes applying a gel that includes salmon thrombin.

16. The method of claim 15, wherein the gel also includes fibrinogen.

17. The method of claim 16, wherein the fibrinogen is salmon fibrinogen.

18. The method of claim 15, wherein the gel also includes any one or more of polyethylene glycol, a synthetic molecule preparation, collagen, and alginates.

19. The method of claim 15, wherein applying the gel includes injecting the gel.

20. The method of claim 13, further comprising obtaining the salmon thrombin using recombinant technology.

21. The method of claim 13, further comprising obtaining the salmon thrombin by fractionation.

22. The method of claim 13, wherein applying salmon thrombin at the neural injury site comprises applying salmon thrombin at the neural injury site as the only blood component.

* * * * *